(12) United States Patent
Gliner

(10) Patent No.: US 9,427,585 B2
(45) Date of Patent: Aug. 30, 2016

(54) SYSTEMS AND METHODS FOR ENHANCING OR OPTIMIZING NEURAL STIMULATION THERAPY FOR TREATING SYMPTOMS OF PARKINSONS DISEASE AND OR OTHER MOVEMENT DISORDERS

(75) Inventor: Bradford Evan Gliner, Sammamish, WA (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 283 days.

(21) Appl. No.: 13/297,688

(22) Filed: Nov. 16, 2011

(65) Prior Publication Data
US 2012/0065700 A1 Mar. 15, 2012

Related U.S. Application Data

(60) Continuation of application No. 12/843,766, filed on Jul. 26, 2010, now abandoned, which is a division of application No. 11/634,523, filed on Dec. 4, 2006, now abandoned, which is a continuation of application No. 10/317,002, filed on Dec. 10, 2002, now Pat. No. 7,236,830.

(51) Int. Cl.
*A61N 1/05* (2006.01)
*A61N 1/36* (2006.01)

(52) U.S. Cl.
CPC ....... *A61N 1/36167* (2013.01); *A61N 1/36067* (2013.01); *A61N 1/36082* (2013.01)

(58) Field of Classification Search
CPC .................... A61N 1/36067; A61N 1/36082
USPC .......................................................... 607/45
See application file for complete search history.

(56) References Cited

U.S. PATENT DOCUMENTS 2,721,316 A 10/1955 Shaw
3,628,193 A 12/1971 Collins
(Continued)

FOREIGN PATENT DOCUMENTS

DE 19750043 5/1999
EP 0214527 3/1987
(Continued)

OTHER PUBLICATIONS

Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).
(Continued)

*Primary Examiner* — Christopher D Koharski
*Assistant Examiner* — Michael D Abreu

(57) ABSTRACT

Systems and methods for treating a neurological disorder comprising determining a first set of neural stimulation parameters capable of treating a first subset of symptoms, determining a second set of neural stimulation parameters capable of treating a second subset of symptoms, and applying a neural stimulation therapy based upon the first set of neural stimulation parameters and the second set of neural stimulation parameters to the patient. The first set of neural stimulation parameters can include electrical stimulation at a first frequency, and the second set of neural stimulation parameters can include electrical stimulation at a second frequency. In other embodiments, a treatment method comprises applying a first neural stimulation therapy to the patient in a continuous or generally continuous manner during a first time interval, and applying a second neural stimulation therapy to the patient in a noncontinuous or interrupted manner following the first time interval.

14 Claims, 6 Drawing Sheets

(56) References Cited

U.S. PATENT DOCUMENTS

| | | |
|---|---|---|
| 3,650,276 A | 3/1972 | Burghele et al. |
| 3,918,461 A | 11/1975 | Cooper |
| 4,030,509 A | 6/1977 | Heilman et al. |
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Arseneault et al. |
| 4,328,813 A | 5/1982 | Ray |
| 4,340,038 A | 7/1982 | McKean |
| 4,431,000 A | 2/1984 | Butler et al. |
| 4,474,186 A | 10/1984 | Ledley et al. |
| 4,542,752 A | 9/1985 | DeHaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,844,075 A | 7/1989 | Liss et al. |
| 4,865,048 A | 9/1989 | Eckerson |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |
| 5,054,906 A | 10/1991 | Lyons |
| 5,063,932 A | 11/1991 | Dahl et al. |
| 5,092,835 A | 3/1992 | Schurig et al. |
| 5,121,754 A | 6/1992 | Mullett |
| 5,143,089 A | 9/1992 | Alt |
| 5,169,384 A | 12/1992 | Bosniak et al. |
| 5,184,620 A | 2/1993 | Cudahy et al. |
| 5,193,540 A | 3/1993 | Schulman et al. |
| 5,215,086 A | 6/1993 | Terry, Jr. et al. |
| 5,224,491 A | 7/1993 | Mehra |
| 5,255,678 A | 10/1993 | Deslauriers et al. |
| 5,263,967 A | 11/1993 | Lyons, III et al. |
| 5,271,417 A | 12/1993 | Swanson et al. |
| 5,282,468 A | 2/1994 | Klepinski |
| 5,299,569 A | 4/1994 | Wernicke et al. |
| 5,304,206 A | 4/1994 | Baker, Jr. et al. |
| 5,314,458 A | 5/1994 | Najafi et al. |
| 5,358,513 A | 10/1994 | Powell, III et al. |
| 5,370,672 A | 12/1994 | Fowler et al. |
| 5,405,375 A | 4/1995 | Ayers et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,464,446 A | 11/1995 | Dreessen et al. |
| 5,520,190 A | 5/1996 | Benedict et al. |
| 5,522,864 A | 6/1996 | Wallace et al. |
| 5,537,512 A | 7/1996 | Hsia et al. |
| 5,540,736 A | 7/1996 | Haimovich et al. |
| 5,549,655 A | 8/1996 | Erickson |
| 5,562,708 A | 10/1996 | Combs et al. |
| 5,575,813 A | 11/1996 | Edell et al. |
| 5,591,216 A | 1/1997 | Testerman et al. |
| 5,593,432 A | 1/1997 | Crowther et al. |
| 5,601,611 A | 2/1997 | Fayram et al. |
| 5,611,350 A | 3/1997 | John |
| 5,628,317 A | 5/1997 | Starkebaum et al. |
| 5,674,251 A | 10/1997 | Combs et al. |
| 5,676,655 A | 10/1997 | Howard, III et al. |
| 5,683,422 A | 11/1997 | Rise |
| 5,702,429 A | 12/1997 | King |
| 5,707,334 A | 1/1998 | Young |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski |
| 5,735,814 A | 4/1998 | Elsberry et al. |
| 5,750,376 A | 5/1998 | Weiss et al. |
| 5,752,979 A | 5/1998 | Benabid |
| 5,769,778 A | 6/1998 | Abrams et al. |
| 5,772,591 A | 6/1998 | Cram |
| 5,782,798 A | 7/1998 | Rise |
| 5,782,873 A | 7/1998 | Collins |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,709 A | 11/1998 | Rise et al. |
| 5,843,148 A | 12/1998 | Gijsbers et al. |
| 5,843,150 A | 12/1998 | Dreessen et al. |
| 5,865,842 A | 2/1999 | Knuth et al. |
| 5,871,517 A | 2/1999 | Abrams et al. |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsh |
| 5,913,882 A | 6/1999 | King |
| 5,916,171 A | 6/1999 | Mayevsky |
| 5,925,070 A | 7/1999 | King et al. |
| 5,938,688 A * | 8/1999 | Schiff ........................ 607/45 |
| 5,938,689 A | 8/1999 | Fischell et al. |
| 5,941,906 A | 8/1999 | Barreras, Sr. et al. |
| 5,964,794 A | 10/1999 | Bolz et al. |
| 5,975,085 A | 11/1999 | Rise |
| 5,978,702 A | 11/1999 | Ward et al. |
| 5,983,140 A | 11/1999 | Smith et al. |
| 6,006,124 A | 12/1999 | Fischell et al. |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,026,326 A | 2/2000 | Bardy |
| 6,035,236 A | 3/2000 | Jarding et al. |
| 6,040,180 A | 3/2000 | Johe |
| 6,042,579 A | 3/2000 | Elsberry et al. |
| 6,052,624 A | 4/2000 | Mann |
| 6,055,456 A | 4/2000 | Gerber |
| 6,057,846 A | 5/2000 | Sever, Jr. |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,095,148 A | 8/2000 | Shastri et al. |
| 6,104,956 A | 8/2000 | Naritoku et al. |
| 6,104,960 A | 8/2000 | Duysens et al. |
| 6,122,548 A | 9/2000 | Starkebaum et al. |
| 6,126,657 A | 10/2000 | Edwards et al. |
| 6,128,537 A | 10/2000 | Rise |
| 6,128,538 A | 10/2000 | Fischell et al. |
| 6,134,474 A | 10/2000 | Fischell et al. |
| 6,152,143 A | 11/2000 | Edwards |
| 6,161,044 A | 12/2000 | Silverstone |
| 6,161,045 A | 12/2000 | Fischell et al. |
| 6,176,242 B1 | 1/2001 | Rise |
| 6,190,893 B1 | 2/2001 | Shastri et al. |
| 6,198,958 B1 | 3/2001 | Ives et al. |
| 6,205,360 B1 | 3/2001 | Carter et al. |
| 6,210,417 B1 | 4/2001 | Baudino et al. |
| 6,221,908 B1 | 4/2001 | Kilgard et al. |
| 6,230,049 B1 | 5/2001 | Fischell et al. |
| 6,236,892 B1 | 5/2001 | Feler |
| 6,246,912 B1 | 6/2001 | Sluijter et al. |
| 6,280,462 B1 | 8/2001 | Hauser et al. |
| 6,301,493 B1 | 10/2001 | Marro et al. |
| 6,319,241 B1 | 11/2001 | King et al. |
| 6,339,725 B1 | 1/2002 | Naritoku et al. |
| 6,353,754 B1 | 3/2002 | Fischell et al. |
| 6,354,299 B1 | 3/2002 | Fischell et al. |
| 6,356,792 B1 | 3/2002 | Errico et al. |
| 6,360,122 B1 | 3/2002 | Fischell et al. |
| 6,366,813 B1 | 4/2002 | DiLorenzo |
| 6,375,666 B1 | 4/2002 | Mische |
| 6,381,496 B1 | 4/2002 | Meadows et al. |
| 6,405,079 B1 | 6/2002 | Ansarinia |
| 6,418,344 B1 | 7/2002 | Rezai et al. |
| 6,427,086 B1 | 7/2002 | Fischell et al. |
| 6,456,886 B1 | 9/2002 | Howard, III et al. |

(56) References Cited

U.S. PATENT DOCUMENTS

| | | |
|---|---|---|
| 6,459,936 B2 | 10/2002 | Fischell et al. |
| 6,463,328 B1 | 10/2002 | John |
| 6,464,356 B1 | 10/2002 | Sabel et al. |
| 6,466,822 B1 | 10/2002 | Pless |
| 6,473,568 B2 | 10/2002 | Kashiyama |
| 6,473,639 B1 | 10/2002 | Fischell et al. |
| 6,480,743 B1 | 11/2002 | Kirkpatrick et al. |
| 6,484,059 B2 | 11/2002 | Gielen |
| 6,487,450 B1 | 11/2002 | Chen |
| 6,499,488 B1 | 12/2002 | Hunter et al. |
| 6,505,075 B1 | 1/2003 | Weiner |
| 6,507,755 B1 | 1/2003 | Gozani et al. |
| 6,529,774 B1 | 3/2003 | Greene |
| 6,556,868 B2 | 4/2003 | Naritoku et al. |
| 6,569,654 B2 | 5/2003 | Shastri et al. |
| 6,591,138 B1 | 7/2003 | Fischell |
| 6,597,954 B1 | 7/2003 | Pless et al. |
| 6,615,065 B1 | 9/2003 | Barrett et al. |
| 6,622,048 B1 | 9/2003 | Mann et al. |
| 6,633,780 B1 | 10/2003 | Berger |
| 6,665,562 B2 | 12/2003 | Gluckman et al. |
| 6,684,105 B2 | 1/2004 | Cohen et al. |
| 6,687,525 B2 | 2/2004 | Llinas et al. |
| 6,690,974 B2 | 2/2004 | Archer et al. |
| 6,708,064 B2 | 3/2004 | Rezai |
| 6,725,094 B2 | 4/2004 | Saberski |
| 6,764,498 B2 | 7/2004 | Mische |
| 6,782,292 B2 | 8/2004 | Whitehurst |
| 6,788,975 B1 | 9/2004 | Whitehurst et al. |
| 6,795,737 B2 | 9/2004 | Gielen et al. |
| 6,810,286 B2 | 10/2004 | Donovan et al. |
| 6,839,594 B2 | 1/2005 | Cohen et al. |
| 6,873,872 B2 | 3/2005 | Gluckman et al. |
| 6,892,097 B2 | 5/2005 | Holsheimer |
| 6,895,280 B2 | 5/2005 | Meadows et al. |
| 6,907,296 B1 | 6/2005 | Doan et al. |
| 6,934,580 B1 | 8/2005 | Osorio et al. |
| 6,944,497 B2 | 9/2005 | Stypulkowski |
| 6,944,501 B1 | 9/2005 | Pless |
| 6,959,215 B2 | 10/2005 | Gliner et al. |
| 6,990,377 B2 | 1/2006 | Gliner et al. |
| 7,006,859 B1 | 2/2006 | Osorio et al. |
| 7,010,351 B2 | 3/2006 | Firlik et al. |
| 7,024,247 B2 | 4/2006 | Gliner et al. |
| 7,110,820 B2 | 9/2006 | Tcheng et al. |
| 2002/0077670 A1 | 6/2002 | Archer et al. |
| 2002/0087201 A1 | 7/2002 | Firlik et al. |
| 2002/0091419 A1 | 7/2002 | Firlik et al. |
| 2002/0099412 A1 | 7/2002 | Fischell et al. |
| 2002/0169485 A1 | 11/2002 | Pless et al. |
| 2003/0074032 A1 | 4/2003 | Gliner |
| 2003/0078633 A1 | 4/2003 | Firlik et al. |
| 2003/0088274 A1 | 5/2003 | Gliner et al. |
| 2003/0097161 A1 | 5/2003 | Firlik et al. |
| 2003/0114886 A1 | 6/2003 | Gluckman et al. |
| 2003/0125772 A1 | 7/2003 | Olson et al. |
| 2003/0125786 A1 | 7/2003 | Gliner et al. |
| 2003/0130706 A1 | 7/2003 | Sheffield et al. |
| 2003/0149457 A1 | 8/2003 | Tcheng et al. |
| 2003/0176901 A1 | 9/2003 | May |
| 2003/0187490 A1 | 10/2003 | Gliner |
| 2003/0187491 A1 | 10/2003 | Greenberg et al. |
| 2004/0073270 A1 | 4/2004 | Firlik et al. |
| 2004/0082847 A1 | 4/2004 | McDermott |
| 2004/0088024 A1 | 5/2004 | Firlik et al. |
| 2004/0092809 A1 | 5/2004 | DeCharms |
| 2004/0102828 A1 | 5/2004 | Lowry et al. |
| 2004/0111127 A1 | 6/2004 | Gliner |
| 2004/0131998 A1 | 7/2004 | Marom et al. |
| 2004/0138550 A1 | 7/2004 | Hartlep et al. |
| 2004/0158298 A1 | 8/2004 | Gliner et al. |
| 2004/0176831 A1 | 9/2004 | Gliner et al. |
| 2004/0181263 A1 | 9/2004 | Balzer et al. |
| 2004/0215287 A1 | 10/2004 | Swoyer et al. |
| 2004/0236388 A1 | 11/2004 | Gielen et al. |
| 2004/0243205 A1 | 12/2004 | Keravel et al. |
| 2004/0249422 A1 | 12/2004 | Gliner et al. |
| 2005/0004620 A1 | 1/2005 | Singhal et al. |
| 2005/0015129 A1 | 1/2005 | Mische |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2005/0182453 A1 | 8/2005 | Whitehurst et al. |
| 2006/0015153 A1 | 1/2006 | Gliner et al. |
| 2006/0106430 A1 | 5/2006 | Fowler et al. |
| 2006/0106431 A1 | 5/2006 | Wyler et al. |
| 2006/0129205 A1 | 6/2006 | Boveja et al. |
| 2006/0173522 A1 | 8/2006 | Osorio |
| 2006/0217782 A1 | 9/2006 | Boveja et al. |

FOREIGN PATENT DOCUMENTS

| | | |
|---|---|---|
| EP | 0319844 | 6/1989 |
| EP | 0998958 | 5/2000 |
| EP | 1145736 | 10/2001 |
| EP | 1180056 | 11/2003 |
| WO | WO 87-007511 | 12/1987 |
| WO | WO 94-007564 | 4/1994 |
| WO | WO 95-021591 | 8/1995 |
| WO | WO 98-006342 | 2/1998 |
| WO | WO 00-007494 | 2/2000 |
| WO | WO 01-093953 | 12/2001 |
| WO | WO 01-097906 | 12/2001 |
| WO | WO 02-009811 | 2/2002 |
| WO | WO 00-040295 | 4/2002 |
| WO | WO 02-036003 | 5/2002 |
| WO | WO 02-038031 | 5/2002 |
| WO | WO 02-038217 | 5/2002 |
| WO | WO 02-073526 | 9/2002 |
| WO | WO 03-043690 | 5/2003 |
| WO | WO 03-082402 | 10/2003 |

OTHER PUBLICATIONS

Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).

Behrens, T. et al., "Non-invasive mapping of connections between human thalamus and cortex using diffusion imaging," Nature neuroscience, vol. 6 No. 7, pp. 750-757 (Jul. 2003).

Bel, S. and Bauer, B.L., "Dorsal Column Stimulation (DCS): Cost to Benefit Analysis," Acta Neurochirurgica, Suppl. 52, pp. 121-123 (1991).

Benabid, A.L. et al., "Chronic electrical stimulation of the ventralis intermedius nucleus of the thalamus as a treatment of movement disorders," J. Neurosurg., Apr. 1997, 86(4); 737; http:--www.ncbi.nlm.nih.gov; [accessed Nov. 18, 2003].

Bezard et al., "Cortical Stimulation and Epileptic Seizure: A Study of the Potential Risk in Primates," Neurosurgery, vol. 45, No. 2, Aug. 1999, 346-350.

Binder, J. M.D., "Functional Magnetic Resonance Imaging: Language Mapping," Neurosurgery Clinics of North America, vol. 8, No. 3, Jul. 1997, pp. 383-392.

Bluestone, Avraham Y. et al., "Three-dimensional optical tomography of hemodynamics in the human head," Optics Express, vol. 9, No. 6, pp. 272-286 (Sep. 10, 2001).

Brain Electrical Stimulation to Enhance Recovery After Stroke, ClinicalTrials.gov, URL: http://www.clinicaltrials.gov/ct/show/NCT00085657?order=2 [Retrieved on Dec. 22, 2005].

(56) References Cited

OTHER PUBLICATIONS

Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).
Bury, Scott et al., "The Effects of Behavioral Demand on Motor Cortical and Cerebellar Structural Plasticity After Brain Injury in Adult Rats," http://www.mcmasterca-inabis98-schallert-bury0827-two.html#introduction, 2 pages [Retrieved on Mar. 1, 2003].
Butefisch et al., "Mechanisms of use-dependent plasticity in the human motor cortex," Proc. Natl. Acad. Sci. USA, vol. 97, No. 7, pp. 3661-3665 (Mar. 2000).
Canavero, S. and Paolotti, R., "Extradural Motor Cortex Stimulation for Advanced Parkinson's Disease: Case Report," Movement Disorders, Jan. 2000, 15(1):169-171.
Cao, Yue et al., "Cortical Language Activation in Stroke Patients Recovering From Aphasia With Functional MRI," Stroke, vol. 30, pp: 2331-2340, Nov. 1999.
Cheun et al., "Differentiation of a Stem Cell Line Toward a Neuronal Phenotype," Int. J. Devl. Neuroscience, vol. 9, No. 4, pp. 391-404 (1991).
Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.
Cincotta et al., "Reorganization of the motor cortex in a patient with congenital hemiparesis and mirror movements," Neurology, Jul. 12, 2000, 5+A535(1), pp. 129-131.
Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.
Classen et al., "Rapid Plasticity of Human Cortical Movement Representation Induced by Practice," The Journal of Neurophysiology, vol. 79, No. 2, pp. 1117-1123 (Feb. 1998).
Cohen et al., "Studies of Neuroplasticity With Transcranial Magnetic Stimulation," The Journal of Clinical Neurophysiology, vol. 15, No. 4 (1998).
Cramer et al., "Use of Functional MRI to Guide Decisions in a clinical Stroke Trial," Stroke, Journal of the American Heart Association, May 2005, pp. e50-e52, American Heart Association, Dallas TX.
Cramer, S.C. and Bastings, E.P., "Mapping clinically relevant plasticity after stroke," Neuropharmacology vol. 19, No. 5, pp. 842-851 (Apr. 2000).
Cytokines Web Clinical Significance, Cytokines Web, 2 pages, Url: http:--cmbi.bjmu.edu.cn-cmbidata-cgf-CGF_Database-cytweb-roles-index.html [Retrieved on Sep. 2, 2005].
Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).
De Ridder, Dirk et al., "Magnetic and electrical stimulation of the auditory cortex for intractable tinnitus," Journal Neurosurg., vol. 100, pp. 560-564, (Mar. 2004).
Di Lazzaro, V. et al., "Theta-burst repetitive transcranial magnetic stimulation suppresses specific excitatory circuits in the human motor cortex," Physiology in Press; published online on Apr. 21, 2005 as 10.1113-jphysiol.2005.087288.
Ding, Yuemin et al., "Neural Plasticity After Spinal Cord Injury," Current Pharmaceutical Design vol. 11, No. 11, pp: 1441-1450, Abstract Only, 1 page (Apr. 2005).
Duncan, Pamela W. et al., "Defining post-stroke recovery: implications for design and interpretation of drug trials," Neuropharmacology vol. 39, pp. 835-841 (2000).
Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam, NL.
Feys et al., "Value of somatosensory and motor evoked potentials in predicting arm recovery after a stroke," (Oct. 1999).

Franzini et al., "Reversal of thalamic hand syndrome by long-term motor cortex stimulation," Journal of Neurosurgery 93(5):873-875, Nov. 2000.
Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.
Fregni, Felipe et al., "Anodal Transcranial Direct Current Stimulation of Prefrontal Cortex Enhances Working Memory," Experimental Brain Research vol. 166, No. 1, pp: 23-30 (Sep. 2005).
Gladstone et al., "Enhancing Recovery after Stroke with Noradrenergic Pharmacotherapy: A New Frontier?" Can J. Neurol. Sci., vol. 27, No. 2, May 2000, pp. 97-105.
Gordon et al., "Parameters for direct cortical electrical stimulation in the human: histopathologic confirmation," Electroencephalography and clinical Neurophysiology, vol. 75, pp. 371-377 (1990).
Hagemann, Georg et al., "Increased Long-Term Potentiation in the Surround of Experimentally Induced Focal Cortical Infarction," Annals of Neurology, vol. 44, No. 2, pp. 255-258 (Aug. 1998).
Haglund, Michael M. et al., "Optical imaging of epileptiform and functional activity in human cerebral cortex," Nature, Aug. 20, 1992, pp. 668-671, vol. 358, Nature Publishing Group.
Hayakawa, Toshiji et al., "Changes in Cerebral Oxygenation and Hemodynamics During Obstructive Sleep Apneas," Chest, vol. 109, pp. 916-921 (1996).
Hodge, Jr., C.J. and Boakye, M., "Biological Plasticity: The Future of Science in Neurosurgery," Neurosurgery, vol. 48, No. 1 (Jan. 2001).
Hoshi, Yoko et al., "Detection of dynamic changes in cerebral oxygenation coupled to neuronal function during mental work in a man," Neuroscience Letters, vol. 150, pp: 5-8 (1993).
Hoshino et al., "Application of multichannel near-infrared spectroscopic topography to physiological monitoring of the cortex during cortical mapping: technical case report," Surgical Neurology, vol. 64, pp. 272-275 (2005).
How Imagent™ Works. ISS Inc., http://www.iss.com-Products-imagent_fmri.html, 1 page [Retrieved on Oct. 14, 2005].
Huang, Ying-Zu et al., "Theta Burst Stimulation of the Human Motor Cortex," Neuron, vol. 45, pp. 201-206 (Jan. 20, 2005).
Hummel, Friedhelm et al., "Effects of non-invasive cortical stimulation on skilled motor function in chronic stroke," Brain Advance Access, pp. 1-10, (Jan. 5, 2005).
Imagent™ Functional Brain Imaging System, ISS, Inc., http://www.iss.com-Products-imagent.html, 2 pages [Retrieved on Oct. 14, 2005].
Imagent™ functional Near Infrared Imaging System (fNIRS) Brain Imaging Using Infrared Photons, ISS Inc., http://www.iss.com-products-imagent-Imagent.pdf, 8 pages [Retrieved on Oct. 14, 2005].
Ishibashi, Tomoko et al., "Astrocytes Promote Myelination in Response to Electrical Impulses," Neuron 49, pp. 823-832, (Mar. 16, 2006).
Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp: 571-577 (Dec. 2003).
Kauhanen et al., "Domains and Determinants of Quality of Life After Stroke Caused by Brain Infarction," Arch. Phys. Med. Rehabil., vol. 81, pp. 1541-1546 (Dec. 2000).
Kelly-Spratt, K. "Transfection of PC-12 cells: a model system for primary neuronal cells," Qiagen News, Customer application article, www.diagen.com, Issue 4, 1998, 2 pages.
Keyvani, Kathy et al., "Suppression of proteasome C2 contralateral to ischemic lesions in rat brain," Brain Research, vol. 858, pp: 386-392, 2000.
Kilgard, Michael et al., "Cortical Map Reorganization Enabled by Nucleus Basalis Activity," Science, vol. 279 pp. 1714-1717 (Mar. 13, 1998).
Kimura et al., "Electrically induced neurite outgrowth of PC12 cells on the electrode surface," Med. Biol. Eng. Comput., Jul. 1998, vol. 36, No. 4, pp. 493-498, Springer Berlin / Heidelberg.

(56) References Cited

OTHER PUBLICATIONS

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kopell et al., "The Continuing Evolution of Psychiatric Neurosurgery," CNS Spectrums, vol. 5, No. 10, pp. 20-31 (Oct. 2000).

Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.

Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

L-DOPA dyskinesias, BioChemistry of PD, http://www.mayo.edu-fdp-pd-info-dyskinesias.htm [Retrieved on Dec. 22, 2005].

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Liepert et al., "Treatment-Induced Cortical Reorganization After Stroke in Humans," Stroke, Jun. 2000, 31(6):1210-1216.

Lutsep et al., "Safety of Cortical Stimulation in Patients with Hemiparetic Stroke," Oasis, Online Abstract Submission and Invitation System—Program Planner, International Stroke Conference 2005, 1 pages, American Stroke Association.

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Mansur, C.G. et al., "A sham stimulation-controlled trial of rTMS of the unaffected hemisphere in stroke patients," Neurology, vol. 64, pp. 1802-1804 (2005).

Martin et al., "Transcranial Magnetic Stimulation as a Complementary Treatment for Aphasia," Semin Speech Language, vol. 25, pp: 181-191 (2004) Abstract Only—1 page.

Martinez et al., "Motor hand recovery after stroke Prognostic yield of early transcranial magnetic stimulation," Electromyogr. Clin. Neurophysiol., Oct.-Dec. 1999, 39(7):405-410.

Meyerson, B.A. et al., "Motor Cortex Stimulation as Treatment of Trigeminal Neuropathic Pain", Acta Neurochirurgica Supplementum, vol. 58, pp: 150-153 (1993).

Misawa et al., "Low-frequency transcranial magnetic stimulation for epilepsia partialis continua due to cortical dysplasia," Journal of the Neurological Sciences, vol. 234, 2005, pp. 37-39.

Motamedi et al., "Optimizing Parameters for Terminating Cortical Afterdischarges with Pulse Stimulation," Epilepsia 43(8):836-846, 2002, Blackwell Publishing, Inc.

Netz et al., "Reorganization of motor output in the non-affected hemisphere after stroke," Brain, 120, pp. 1579-1586 (1997).

Nitsche, M.A. and Paulus, W., "Excitability changes induced in the human motor cortex by weak transcranial direct current stimulation," The Journal of Physiology, Sep. 15, 2000, 527(3):633-9.

Nitsche, Michael A. et al. "Facilitation of Implicit Motor Learning by Weak Transcranial Direct Current Stimulation of the Primary Motor Cortex in the Human," Journal of Cognitive Neuroscience, May 2003, 15(4):619-26, Published by the MIT Press with the Cognitive Neuroscience Institute.

Nitsche, Michael A. et al., "Level of action of cathodal DC opographyn induced inhibition of the human motor cortex," Dec. 2, 2002, Clinical Neurophysiology 114 (2003) 600-604.

Nudo, Randolph J. et al., "Recovery after damage to motor cortical areas," Current Opinion in Neurobiology, vol. 9, Issue 6, pp: 740-747, Dec. 1, 1999.

Oliveri et al., "Paired transcranial magnetic stimulation protocols reveal a pattern of inhibition and facilitation in the human parietal cortex," The Journal of Physiology, Dec. 1, 2000, 529.2, pp. 461-468.

Panchanathan, Sethuraman et al., "Rehabilitation of patients with hemispatial neglect using visual-haptic feedback in Virtual reality environment," http://www.public.asu.edu~tmcdani-publications.htm, 5 pages [Retrieved on Dec. 22, 2005].

Pascual-Leone et al., "Study and Modulation of Human Cortical Excitability With Transcranial Magnetic Stimulation," Journal of Clinical Neurophysiology, Jul. 1998, 15(4):333-43, Published by Lippincott Williams & Wilkins.

Pascual-Leone et al., "Transcranial magnetic stimulation and neuroplasticity," Neuropshychologia, Feb. 1999, 37(2):207-17.

Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimulation," Neuron, vol. 45, pp. 181-183 (Jan. 20, 2005).

Penn, Michael, "Stemming Parkinson's," On Wisconsin Alumni Magazine, Summer 2003, http://www.uwalumni.com-onwisconsin-2003_summer-research.html, 1 page [Retrieved on Dec. 22, 2005].

Politis, M. J., "Mammalian Optic Nerve Regeneration Following the Application of Electric Fields," The Journal of Trauma, Nov. 1988, vol. 28, No. 11, pp. 1548-1552.

Price, J. et al., "Neurotransplantation in neurodegenerative disease: a survey of relevant issues in developmental neurobiology," Novartis Foundation Symposium 231, 2000, pp. 148-165, Wiley, Chichester, UK. [Published Online: Sep. 26, 2003].

Rezai, "Neurostimulation," Neurological Research, vol. 22, No. 3 pp. 235-273 (Apr. 2000).

Robinson, Kenneth R., "The Responses of Cells to Electrical Fields: A Review," The Journal of Cell Biology, vol. 101, pp. 2023-2027 (Dec. 1985).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 48, No. 3 (Mar. 2001).

Saitou et al., "Cerebral Blood Volume And Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sandkuhler, "Learning and memory in pain pathways," Pain, Nov. 2000, 88(2):113-18, Elsevier/North-Holland.

Sanes, "The Relation between Human Brain Activity and Hand Movements," NeuroImage, May 2000, 11(5), pp. 370-374.

Sanes, J. and Donoghue, J.P., "Plasticity and Primary Motor Cortex," Annual Review of Neuroscience, 2000, 23:393-415.

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

Schiff et al., "A neuromodulation strategy for rational therapy of complex brain injury states," Neurological Research, vol. 22 pp. 267-272 (Apr. 2000).

SCIRun, Scientific Computing and Imaging Institute. http://www.sofware.sci.utah.edu-scirun.html, 2 pages [Retrieved on Jul. 24, 2005].

Shimizu et al., "Therapeutic efficacy of transcranial magnetic stimulation for hereditary spinocerebellar degeneration," Tohoku Journal of Experimental Medicine, 189(3):203-11 (Nov. 1999).

Siebner et al., "Lasting cortical activation after repetitive TMS of the motor cortex," Neurology 54, pp. 956-963 (Feb. 2000).

Sioutos et al. Continuous Regional Cerebral Cortical Blood Flow Monitoring in Head-injured Patients, Neurosurgery, vol. 36, No. 5, May 1995, pp. 943-949.

(56) References Cited

OTHER PUBLICATIONS

Stefan et al., "Induction of plasticity in the human motor cortex by paired associative stimulation," Brain, vol. 123, No. 3, pp. 572-584 (Mar. 2000).

Strangman, Gary et al., "A Quantitative Comparison of Simultaneous Bold fMRI and NIRS Recordings during Functional Brain Activation," NeuroImage, vol. 17, pp: 719-731 (2002).

Strangman, Gary et al., "Factors affecting the accuracy of near-infrared spectroscopy concentration calculations for focal changes in oxygenation parameters," NeuroImage, vol. 18, pp: 865-879 (2003).

Strangman, Gary et al., "Non-Invasive Neuroimaging Using Near-Infrared Light," Biological Psychiatry, vol. 52, pp: 679-693 (2002).

Strens, Lucy et al., "The Ipsilateral Human Motor Cortex Can Functionally Compensate for Acute Contralateral Motor Cortex Dysfunction," Current Biology, vol. 13, pp. 1201-1205 (Jul. 15, 2003).

Taga, Gentaro et al., "Brain imaging in awake infants by near-infrared optical topogrpahy," PNAS, vol. 100, No. 19, pp. 10722-10727 (Sep. 16, 2003).

Tang, Cha-Min et al., "Optical Coherence Tomography of the Human Basal Ganglion," Deep Brain Stimulation Consortium Meeting Program Book, Sep. 29-30, 2003, Washington DC.

The GES 250 for Dense-Array Eeg Research, Electrical Geodesics, Inc., http://www.egi.com/ges250r_n.html, 3 pages [Retrieved on Aug. 25, 2005].

The INVOS Cerebral Oximeter, Somanetics, http://www.somanetics.net/invos.htm, 1 pages [retrieved from the internet on Dec. 22, 2005].

The National Institutes of Health (NIH) Consensus Development Program, "Surgery for Epilepsy," National Institutes of Health Consensus Development conference Statement, Mar. 19-21, 1990, 16 pages.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Timmermann, Lars et al., "The cerebral oscillatory network of parkinsonian resting tremor," Brain, vol. 126, pp. 199-212, (2003).

Toronov, Vlad et al., "Near-infrared study of fluctuations in cerebral hemodynamics during rest and motor stimulation: Temporal analysis and spatial mapping," Medical Physics, vol. 27, No. 4, pp: 801-815 (Apr. 2000).

Tractography, Absolute Astronomy Reference, http://www.absoluteastronomy.com-encyclopedia-T-Tr-Tractography.htm, 2 pages [Retrieved on Jul. 24, 2005].

Tsubokawa, T. et al., "Chronic Motor Cortex Stimulation for the Treatment of Central Pain," Acta Neurochirurgica, Supplementum. vol. 52, pp. 137-139 (1991).

Tsubokawa, T. et al., "Chronic Motor Cortex Stimulation in Patients with Thalamic Pain," J. Neurosurg 78:393-401, (Mar. 1993).

Tsubokawa, T. et al., "Treatment of Thalamic Pain by Chronic Motor Cortex Stimulation", PACE, vol. 14, pp. 131-134 (Jan. 1991).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Turton et al., "Contralateral and ipsilateral EMG responses to transcranial magnetic stimulation during recovery of arm and hand function after stroke," Electroencephalography and Clinical Neurophysiology, Aug. 1996, 101(4):316-28, Elsevier.

Turton, A. and Lemon, R.N., "The contribution of fast corticospinal input to the voluntary activation of proximal muscles in normal subjects and in stroke patients," Exp. Brain Res., Dec. 1999, 129(4):559-572, Springer Berlin / Heidelberg.

Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, May-Jun. 2000, 31(3):304-315, Elsevier Science, Inc.

Velasco et al., "Electrical Stimulation for Epilepsy: Stimulation of Hippocampal Foci," Proceedings of the 13th Meeting of the World Society for Stereotactic and Functional Neurosurgery, Sep. 11-14, 2001, Stereotactic and Functional Neurosurgery, vol. 77, No. 14, 2001, pp. 223-227.

Velasco et al., "Subacute and Chronic Electrical Stimulation of the Hippocampus on Intractable Temporal Lobe Seizures: Preliminary Report," Archives of Medical Research, May-Jun. 2000, 31(3):316-28, Elsevier Science.

Velasco et al., "Subacute Electrical Stimulation of the Hippocampus Blocks Intractable Temporal Lobe Seizures and Paroxysmal EEG Activities," Epilepsia, Feb. 2000, 41(2):158169, Lippincott Williams & Wilkins, Philadelphia.

Walker-Batson et al., "Amphetamine Paired With Physical Therapy Accelerates Motor Recovery After Stroke," Stroke, vol. 26, No. 12, pp. 2254-2259 (1995).

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, aans.org, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectormy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005, aans.org, http://www.aans.org/Library/Article.aspx?Articleld=24934, 2 pages.

Weinand, Martin E. et al., "Cerebral blood flow and temporal lobe epileptogenicity," Retrieved from the Internet on Dec. 22, 2005, http://www.aans.org/education/journal/neurosurgical/nov96/1-5-3.asp, 13 pages.

Woodbury, D. et al., "Adult Rat and Human Bone Marrow Stromal Cells Differentiate Into Neurons," Journal of Neuroscience Research, Aug. 15, 2000, 61(4):364-70, Wiley Interscience, New York, NY.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

Yokoh, Arika et al., "Intermittent versus continuous brain retraction," Journal of Neurosurgery, vol. 58, pp. 918-923 (Jun. 1983).

Ziemann et al., "Modulation of Plasticity in Human Motor Cortex after Forearm Ischemic Nerve Block," The Journal of Neuroscience 18(3):1115-1123 (Feb. 1998).

European Search Report for Patent Application No. 03790492.7; Northstar Neuroscienc, Inc.; Feb. 26, 2008; 4 pgs; European Patent Office.

Durand, Dominique M. et al., "Desynchronization of epileptiform activity by extracellular current pulses in rat hippocampal slices," J Physiol. 1994;480.3:527-537.

Saint-Cyr, Jean A. Ph.D et al., "Localization of clinically effective stimulating electrodes in the human subthalamic nucleus on magnetic resonance imaging," J Neurosurg. 2002;97:1152-1166.

(56) References Cited

OTHER PUBLICATIONS

Tass, Peter A., "Desynchronizing double-pulse phase resetting and application to deep brain stimulation," Biol Cybern. 2001;85:343-354.

Titcombe, Michele S. et al., "Dynamics of Parkinsonian tremor during deep brain stimulation," CHAOS. 2001;11(4):766-773.

* cited by examiner

SYSTEMS AND METHODS FOR ENHANCING OR OPTIMIZING NEURAL STIMULATION THERAPY FOR TREATING SYMPTOMS OF PARKINSONS DISEASE AND OR OTHER MOVEMENT DISORDERS

CROSS-REFERENCE TO RELATED APPLICATION(S)

This application is a continuation of U.S. application Ser. No. 12/843,766, filed Jul. 26, 2010, now abandoned, which is a divisional of U.S. application Ser. No. 11/634,523, filed Dec. 4, 2006, now abandoned, which is a continuation of U.S. application Ser. No. 10/317,002, filed Dec. 10, 2002, now U.S. Pat. No. 7,236,830, the disclosures of which are incorporated herein by reference.

TECHNICAL FIELD

The present disclosure relates generally to systems and methods for treating symptoms of Parkinson's Disease and/or other movement disorders. More particularly, the present disclosure describes a system and method for enhancing or optimizing the effectiveness of neural stimulation in treating the symptoms of movement disorders such as Parkinson's Disease.

BACKGROUND

A wide variety of mental and physical processes are controlled or influenced by neural activity in particular regions of the brain. For example, various physical or cognitive functions are directed or affected by neural activity within the sensory or motor cortices. Across most individuals, particular areas of the brain appear to have distinct functions. In the majority of people, for example, the areas of the occipital lobes relate to vision; the regions of the left interior frontal lobes relate to language; portions of the cerebral cortex appear to be consistently involved with conscious awareness, memory, and intellect; and particular regions of the cerebral cortex as well as the basal ganglia, the thalamus, and the motor cortex cooperatively interact to facilitate motor function control.

Many problems or abnormalities with body functions can be caused by damage, disease, and/or disorders in the brain. For example, Parkinson's Disease (PD) is related to the degeneration or death of dopamine producing neurons in the substantia nigra region of the basal ganglia in the brain. Dopamine is neurotransmitter that transmits signals between areas of the brain. As the neurons in the substantia nigra deteriorate, the reduction in dopamine causes abnormal neural activity that results in a chronic, progressive deterioration of motor function control. Conservative estimates indicate that PD may affect more than one million individuals in the United States alone.

PD patients typically exhibit one or more of four primary symptoms. One primary symptom is a tremor in an extremity (e.g., a hand) that occurs while the extremity is at rest. Other primary symptoms include a generalized slowness of movement (bradykinesia); increased muscle rigidity or stiffness (rigidity); and gait or balance problems (postural dysfunction). In addition to or in lieu of these primary symptoms, PD patients may exhibit secondary symptoms including: difficulty initiating or resuming movements; loss of fine motor skills; lack of arm swing on the affected side of the body while walking; foot drag on the affected side of the body; decreased facial expression; voice and/or speech changes; cognitive disorders; feelings of depression or anxiety; and/or other symptoms.

Effectively treating PD or other movement disorders related to neurological conditions can be very difficult. Current treatments for PD symptoms include drugs, ablative surgical intervention, and/or neural stimulation. Drug treatments or therapies may involve, for example, the administration of a dopamine precursor that is converted to dopamine within the central nervous system (i.e., Levodopa (L-dopa)). Other types of drug therapies are also available. Unfortunately, drug therapies frequently become less effective or ineffective over time for an undesirably large patient population. A PD patient may require multiple drugs in combination to extend the time period of efficacy of drug therapies. Drug treatments additionally have a significant likelihood of inducing undesirable physical side effects; motor function complications such as uncontrollable involuntary movements (dyskinesias) are a particularly common side effect. Furthermore, drug treatments may induce undesirable cognitive side effects such as confusion and/or hallucinations.

Ablative surgical intervention for PD typically involves the destruction of one or more neural structures within the basal ganglia or thalamus that have become overactive because of the lack of dopamine. Unfortunately, such neural structures reside deep within the brain, and hence ablative surgical intervention is a very time consuming and highly invasive procedure. Potential complications associated with the procedure include risk of hemorrhage, stroke, and/or paralysis. Moreover, because PD is a progressive disease, multiple deep brain surgeries may be required as symptoms progressively worsen over time. Although ablative surgical intervention may improve a PD patient's motor function, it is not likely to completely restore normal motor function. Furthermore, since ablative surgical intervention permanently destroys neural tissue, the effects of such intervention cannot be readily adjusted or "fine tuned" over time.

Neural stimulation treatments have shown promising results for reducing some of the symptoms associated with PD. Neural activity is governed by electrical impulses or "action potentials" generated in and propagated by neurons. While in a quiescent state, a neuron is negatively polarized and exhibits a resting membrane potential that is typically between −70 and −60 mV. Through chemical connections known as synapses, any given neuron receives excitatory and inhibitory input signals or stimuli from other neurons. A neuron integrates the excitatory and inhibitory input signals it receives, and generates or fires a series of action potentials in the event that the integration exceeds a threshold potential. A neural firing threshold, for example, may be approximately −55 mV. Action potentials propagate to the neuron's synapses and are then conveyed to other synaptically connected neurons.

Neural activity in the brain can be influenced by neural stimulation, which involves the application of electrical and/or magnetic stimuli to one or more target neural populations within a patient using a waveform generator or other type of device. Various neural functions can thus be promoted or disrupted by applying an electrical current to one or more regions of the brain. As a result, researchers have attempted to treat certain neurological conditions, including PD, using electrical or magnetic stimulation signals to control or affect brain functions.

Deep Brain Stimulation (DBS) is a stimulation therapy that has been used as an alternative to drug treatments and ablative surgical therapies. In DBS, one or more electrodes are surgically implanted into the brain proximate to deep brain or subcortical neural structures. For treating PD or other movement disorders, the electrodes are positioned in or proximate to the ventrointermediate nucleus of the thalamus; basal ganglia structures such as the globus pallidus internalis (GPi); or the Subthalamic Nucleus (STN). The location of the stimulation site for the electrodes depends upon the symptoms that a patient exhibits and the severity of the symptoms.

In a typical DBS system, a pulse generator delivers a continuous or essentially continuous electrical stimulation signal having a pulse repetition frequency of approximately 100 Hz to each of two deep brain electrodes. The electrodes are bilaterally positioned on the left and right sides of the brain relative to particular neural structures such as those indicated above. U.S. Pat. No. 5,883,709 discloses one conventional DBS system for treating movement disorders.

Although DBS therapies may significantly reduce one or more PD symptoms, particularly when combined with drug treatments, they are highly invasive procedures. In general, configuring a DBS system to properly function within a patient requires two time consuming, highly invasive surgical procedures for implanting the DBS electrodes. Each such surgical procedure has essentially the same risks as those described above for ablative surgical intervention. Moreover, DBS may not provide relief from some movement disorders.

Motor Cortex Stimulation (MCS) is another type of brain stimulation treatment that has been proposed for treating movement disorders. MCS involves the application of stimulation signals to the motor cortex of a patient. One MCS system includes a pulse generator connected to a strip electrode that is surgically implanted over a portion of only the motor cortex (precentral gyrus). The use of MCS to treat PD symptoms is described in Canavero, Sergro, *Extradural Motor Cortex Stimulation for Advanced Parkinson's Disease: Case Report*, Movement Disorders (Vol. 15, No. 1, 2000).

Because MCS involves the application of stimulation signals to surface regions of the brain rather than deep neural structures, electrode implantation procedures for MCS are significantly less invasive and time consuming than those for DBS. As a result, MCS may be a safer and simpler alternative to DBS for treating PD symptoms. Present MCS techniques, however, fail to address or adequately consider a variety of factors that may enhance or optimize the extent to which a patient experiences short term and/or long term relief from PD symptoms.

DETAILED DESCRIPTION

The following disclosure describes neural stimulation systems and methods for enhancing or optimizing the extent to which a patient may experience relief from symptoms associated with Parkinson's Disease (PD), other movement or motor disorders, and/or various neurological disorders that may have multiple types of symptoms. Such symptoms may include, for example, tremor, rigidity, bradykinesia, postural dysfunction, spasticity, speech deficits, visual disturbances, olfactory deficits, cognitive deficits, memory deficits, emotional or psychiatric disturbances, paresis, pain and/or other symptoms.

Different symptoms may respond to neural stimulation in different manners, and/or across different time scales. For example, neural stimulation optimized to beneficially affect tremor and/or rigidity to a significant degree may provide less significant or minimal benefit relative to other symptoms such as postural dysfunction. Additionally, neural stimulation that has a nearly immediate or reasonably rapid effect upon tremor and/or rigidity may have a significantly or greatly delayed effect upon other symptoms such as bradykinesia. Systems and/or methods described herein may facilitate enhancement or optimization of neural stimulation therapy for treating multiple patient symptoms that may exhibit different treatment response characteristics and/or different response timeframes.

Neural stimulation may facilitate or effectuate neuroplastic changes within a patient's brain, for example, in a manner described in U.S. application Ser. No. 09/802,808, which is incorporated herein by reference. Neuroplastic changes can include adaptive structural changes or reorganizations in particular brain regions, which may result in enhancement or restoration of one or more functional abilities (i.e., physical, sensory, and/or cognitive functions) associated with such brain regions, possibly on a long term or lasting basis. Application of neural stimulation to a patient in accordance with the principles described herein may increase the likelihood that neuroplastic changes can occur to facilitate at least partial recovery of diminished or lost functionality associated with or giving rise to one or more patient symptoms. Such functional recovery may itself reduce the extent to which the patient requires neural stimulation and/or other therapy on an ongoing basis.

Figure 1:
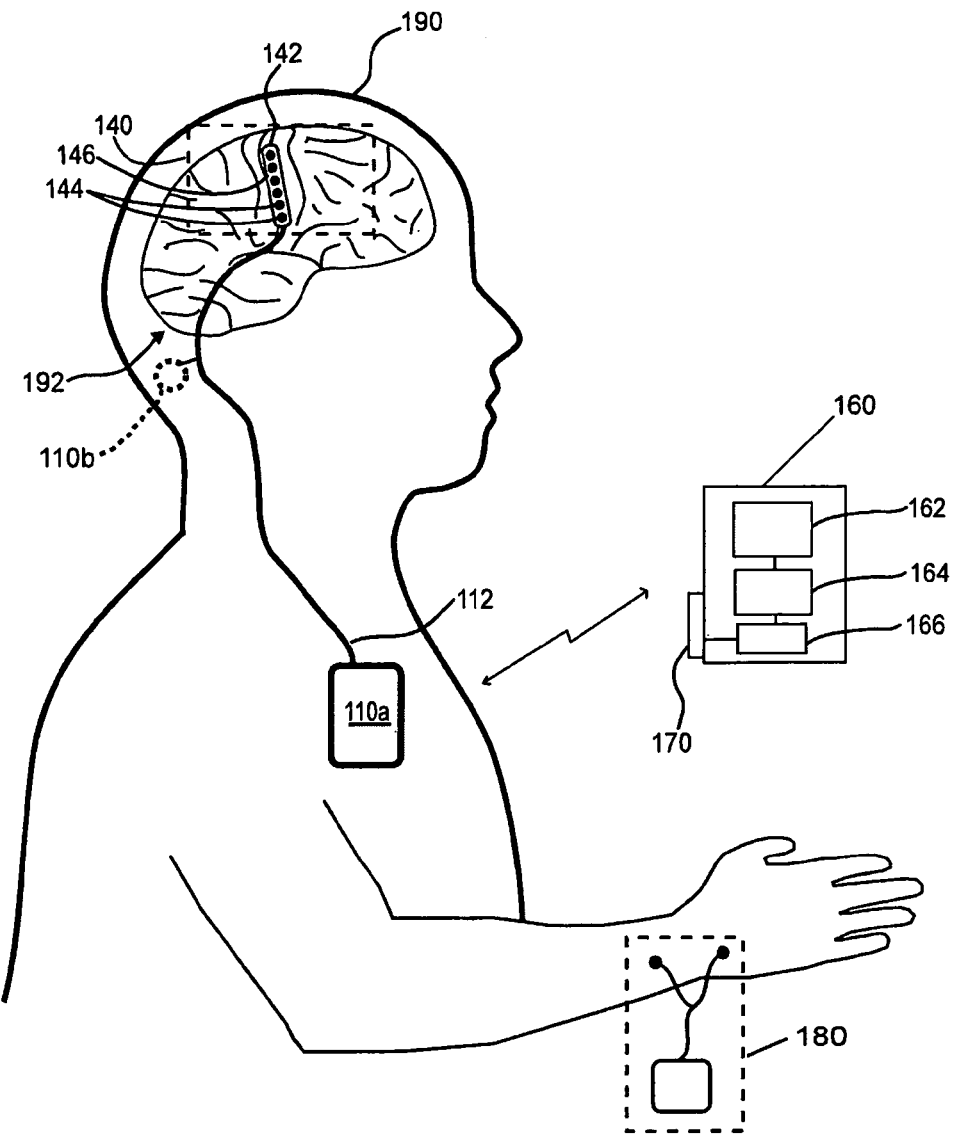
FIG. 1 is a schematic illustration of a neural stimulation system for treating symptoms of Parkinson's Disease and/or other neurological disorders according to an embodiment of the invention.

FIG. 1 is a schematic illustration of a neural stimulation system 100 for treating symptoms of PD and/or other disorders according to an embodiment of the invention. In one embodiment, the neural stimulation system 100 comprises a pulse generator 110a configured to deliver stimulation signals to a patient 190 using a set of electrodes 140. The pulse generator 110a may be coupled to the set of electrodes 140 by one or more leads 112. The pulse generator 110a may further be configured for wireless and/or wire-based communication with a programming unit 160. Depending upon embodiment details, the system 100 may further include one or more patient monitoring units 180 configured to detect, monitor, indicate, measure, and/or assess the severity of particular types of patient symptoms.

The set of electrodes 140 may include one or more cortical electrodes 142 configured to provide, deliver, and/or apply stimulation signals to particular cortical regions of the patient's brain 192 and/or neural populations synaptically connected and/or proximate thereto. A cortical electrode 142 may include one or more electrically conductive contacts 144 carried by a substrate 146 in a manner understood by those skilled in the art. The set of electrodes 140 may alternatively or additionally include one or more penetrating, depth, and/or deep brain electrodes. The set of electrodes 140 may further include or provide one or more stimulation signal return electrodes (i.e., electrodes that provide a current return path) that may be positioned relative to a variety of locations within and/or upon the patient's body.

The characteristics and/or placement of the set of electrodes 140 may depend upon the nature of patient's underlying disorder(s) and/or the type and/or severity of symptoms that the patient 190 experiences or exhibits. In one embodiment, one or more portions of the set of electrodes 140 may be surgically implanted to deliver stimulation signals to target neural populations within the patient's brain in a manner described in U.S. Provisional Application No. 60/432,073, entitled "System and Method for Treating Parkinson's Disease and Other Movement Disorders," filed on Dec. 9, 2002 (Perkins Coie Docket No. 33734.8040US00).

The pulse generator 110*a* may comprise hardware and/or software for generating and outputting stimulation signals to the set of electrodes 140 in accordance with internal instruction sequences and/or in response to control signals, commands, instructions, and/or other information received from the programming unit 160. The pulse generator 110*a* may include a power supply, a pulse unit, a control unit, a programmable computer medium, and a communication unit. The power supply may comprise a battery or other type of power storage device. The pulse unit may comprise circuitry for generating pulse sequences that may be defined or characterized in accordance with various stimulation signal parameters, which are further described below with reference to FIG. 2, The control unit may comprise hardware and/or software configured to direct or manage the local operation of the pulse generator 110*a*, The communication unit may comprise a user interface that facilitates communication with devices external to the pulse generator 110*a*, for example, through telemetric signal transfer. The programmable computer medium may comprise hardware and/or memory resident software. The programmable computer medium may store operational mode information and/or program instruction sequences that may be selected and/or specified in accordance with information received from the programming unit 160. The pulse generator 110*a* may be configured to deliver stimulation signals to particular electrodes 142 and/or specific electrical contacts 144 within the set of electrodes 140 on a selective basis at any given time, in a manner identical, essentially identical, or analogous to that described in U.S. application Ser. No. 09/978,134, which is incorporated herein by reference.

Each element of the pulse generator 110*a* may be incorporated or embedded into a surgically implantable case or housing. Depending upon embodiment details, the pulse generator 110*a* may be surgically implanted into the patient 190 in a subclavicular location. Alternatively, a pulse generator 110*b* may be surgically implanted above the patient's neck, for example, in a skull location posterior to the patient's ear and/or proximate to an electrode implantation site. A surgically formed tunnel or path may route the set of leads 112 that couple the pulse generator 110*a*, 110*b* to the set of electrodes 140, in a manner understood by those skilled in the art. Additionally, one or more electrically conductive portions of the pulse generator's case or housing may serve as a return electrode for electrical current.

The programming unit 160 may comprise a device configured to communicate control signals, commands, instructions, and/or other information to the pulse generator 110*a*. The programming unit 160 may additionally be configured to receive information from the pulse generator 110*a*. Communication between the programming unit 160 and the pulse generator 110*a* may facilitate or effectuate specification, selection, and/or identification of operational modes, instruction sequences, and/or procedures for treating symptoms of PD and/or other neurological disorders in accordance with the present invention, as described in detail below with reference to FIGS. 3 through 6.

In one embodiment, the programming unit 160 includes a processing unit 162, a programmable computer medium 164, and a communication unit 166. The programmable computer medium 164 may store an operating system, program instructions, and/or data, and may comprise various types of hardware and memory resident software, including volatile and/or nonvolatile memory as well as one or more data storage devices. The communication unit 166 may include a wire-based and/or wireless telemetry interface 170 that employs magnetic, radio frequency (RF), and/or optical signaling techniques to communicate with the pulse generator 110*a*. The communication unit 166 may additionally or alternatively include one or more wire-based and/or wireless interfaces that facilitate communication with other devices such as a computer.

A patient monitoring unit 180 may comprise essentially any type of device, subsystem, and/or system configured to detect, monitor, indicate, measure, and/or assess the severity of one or more types of patient symptoms associated with PD and/or other neurological disorders. For example, a patient monitoring unit 180 may comprise a motion detection system configured to detect patient movement associated with tremor. A motion detection system may include light emitting and/or detecting devices and/or accelerometers coupled to particular patient extremities. As another example, a patient monitoring unit 180 may comprise an Electromyography (EMG) system that includes a set of surface or depth electrodes positioned relative to particular muscle groups for detecting electrical signals corresponding to muscle fiber innervation. As another example, a patient monitoring unit 180 may comprise an Electroencephalograpy (EEG) system. As yet another example, a patient monitoring unit 180 may comprise a neural imaging system. As a final example, a patient monitoring unit 180 may comprise one or more electrodes and/or probes (e.g., cerebral bloodflow monitors) positioned upon, proximate, and/or within given target neural populations, and associated hardware and/or software for detecting, presenting, and/or analyzing signals received therefrom.

Figure 2:
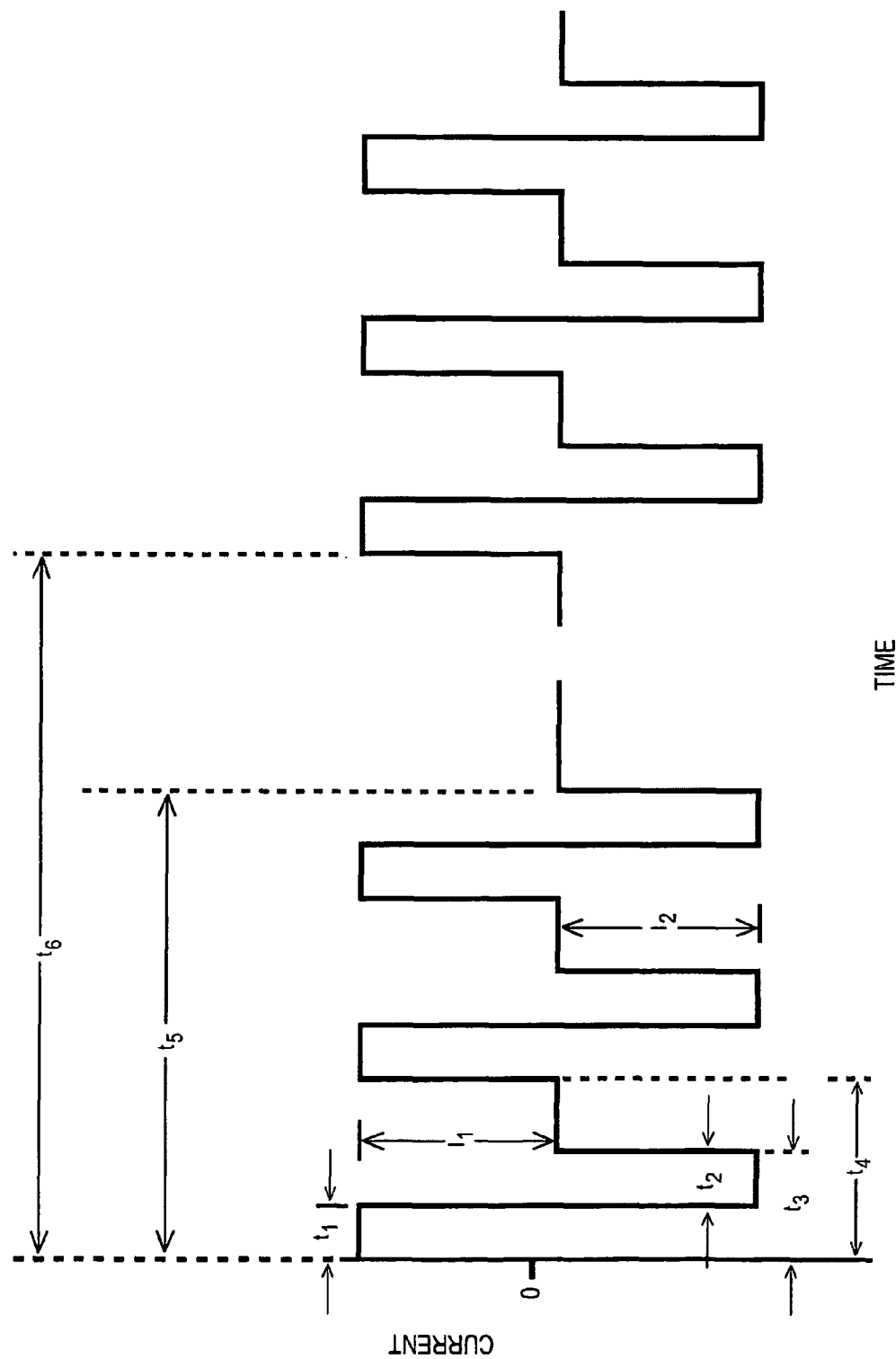
FIG. 2 is a graph illustrating several stimulation parameters that may define, describe, or characterize stimulation signals.

As previously indicated, the pulse generator 110*a* generates and outputs stimulation signals. In the context of the present invention, stimulation signals may comprise electromagnetic pulse sequences. Any given pulse sequence may comprise at least one, and possibly multiple, pulse trains, which may be separated by quiescent intervals. FIG. 2 is a graph illustrating several stimulation parameters that may define, describe, or characterize a pulse train. A stimulus start time $t_0$ defines an initial point at which a pulse train is applied to one or more elements within the set of electrodes 140. In one embodiment, the pulse train may be a biphasic waveform comprising a series of biphasic pulses, and which may be defined, characterized, or described by parameters including a pulse width $t_1$ for a first pulse phase; a pulse width $t_2$ for a second pulse phase; and a pulse width $t_3$ for one or more biphasic pulses. The parameters can also include a pulse repetition rate $1/t_4$ corresponding to a pulse repetition frequency; a pulse duty cycle equal to $t_3$ divided by $t_4$; a pulse burst time $t_5$ that defines a number of pulses in a pulse train; and/or a pulse train repetition rate $t_6$. Other parameters include a peak current intensity or amplitude $I_1$ for a first pulse phase and a peak current intensity $I_2$ for a second pulse phase.

In various embodiments, the pulse width of successive pulses and/or successive pulse phases may vary, such that the pulse repetition frequency within a pulse train and/or a pulse sequence is a function of time. A pulse train having a frequency that varies in time may give rise to a "chirped" frequency profile. Additionally or alternatively, the pulse intensity or amplitude may decay during the first and/or second pulse phases, and the extent of such decay may differ across successive or subsequent pulse phases. Those skilled in the art will understand that a pulse may be a charge-balanced waveform, and that in an alternate embodiment, pulses can be monophasic or polyphasic. Additional stimulation parameters may specify manners in which pulse trains are applied to selected configurations of elements within the set of electrodes 140, such as particular electrodes 142 and/or contacts 144, at any given time.

As defined herein, a test protocol may define or specify neural stimulation parameters associated with one or more pulse sequences to be applied to a patient 190 across or within a given test period duration that may include one or more neural stimulation delivery periods and possibly one or more quiescent periods during which the patient 190 receives no neural stimulation. A test protocol may further define or specify a spatial and/or temporal distribution of elements within the set of electrodes 140 to which neural stimulation may be applied during one or more portions of the test period; and corresponding signal polarities corresponding to particular elements within the set of electrodes 140 relative to one or more portions of the test period. Neural stimulation delivered in accordance with a test protocol comprises a test therapy.

Figure 3:
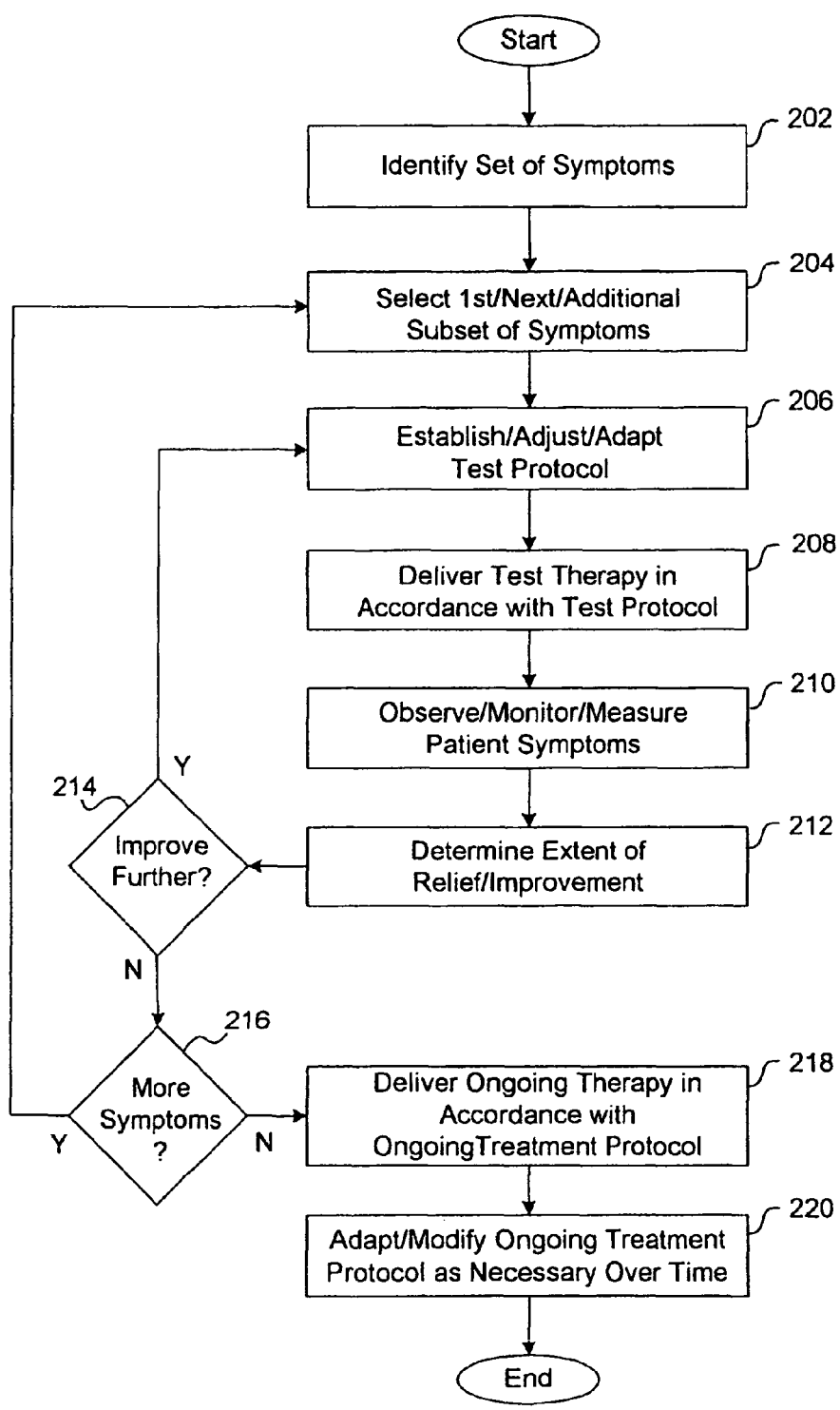
FIG. 3 is a flowchart illustrating various methods for refining, enhancing, or optimizing neural stimulation therapy for treating symptoms of Parkinson's Disease and/or other movement disorders according to an embodiment of the invention.

FIG. 3 is a flowchart illustrating various methods for refining, enhancing, or optimizing neural stimulation therapy for treating symptoms of PD and/or other neurological disorders according to an embodiment of the invention. In one embodiment, a method 200 includes an identification procedure 202 that involves identification of one or more patient symptoms to which neural stimulation therapy, possibly in conjunction with one or more adjunctive therapies, may be directed. The method 200 may also include a symptom selection procedure 204 that involves selection or consideration of a first, a next, or an additional subset of patient symptoms to which neural stimulation therapy may be directed. The symptom selection procedure 204 may facilitate initial selection of symptoms expected to rapidly respond to neural stimulation, such as tremor and/or rigidity, followed by selection of other symptoms such as bradykinesia that may respond more slowly.

The method 200 may further include a test protocol management procedure 206 that involves establishing, adjusting, and/or adapting a test protocol that specifies or defines a test therapy intended to be applied to the patient 190 for a given test period. The test protocol may specify or define neural stimulation parameters corresponding to the test therapy, and may also specify parameters corresponding to one or more adjunctive therapies such as drug therapies.

The method 200 may additionally include a test delivery procedure 208 that involves application or delivery of the test therapy to the patient 190 in accordance with the test protocol; and an observation procedure 210 that involves observation, monitoring, and/or measuring of patient symptoms at one or more times in association with and/or following the delivery procedure 208. The observation procedure 210 may involve one or more patient monitoring units 180, and/or direct human observation of the patient 190.

The method 200 may further include an evaluation procedure 212 involving determination of an extent to which one or more patient symptoms currently under consideration have improved or changed as a result of the most recently applied test therapy. In a manner analogous to that for the observation procedure 210, the evaluation procedure 212 may involve one or more patient monitoring units 180 and/or direct human evaluation of the patient 190. In the event that further improvement of symptoms currently under consideration is necessary, likely, or possible, the method 200 may return to the test protocol management procedure 206. Alternatively, in the event that additional patient symptoms require consideration, the method 200 may return to the symptom selection procedure 204.

In addition to procedures directed toward refining, enhancing, or optimizing an extent to which one or more symptoms can be successfully or adequately treated by neural stimulation (possibly in conjunction with one or more adjunctive therapies), the method 200 may include an ongoing treatment delivery procedure 218 that involves application of an arrived-at ongoing therapy to the patient in accordance with an ongoing, essentially ongoing, or generally ongoing treatment protocol. The ongoing treatment protocol may correspond to or be based upon a previously considered test protocol, and may involve one or more adjunctive therapies. In particular, the ongoing treatment protocol may be identical or essentially identical to a recently considered test protocol, with the exception that an ongoing treatment duration corresponding to the ongoing treatment protocol may be significantly longer than that of the test period corresponding to such a test therapy.

The method 200 may also include a reevaluation procedure 220 that involves a one-time, occasional, or periodic reevaluation, adjustment, and/or adaptation of a most recent ongoing treatment protocol in view of potential or likely neuroplastic changes, variations in ongoing treatment effectiveness, and/or overall patient health or condition over time. Such reevaluation, adjustment, or adaptation may occur after a predetermined time interval, such as 1 month, several months, or 1 or more years following initiation of an ongoing treatment delivery procedure 218. The reevaluation procedure 220 may be performed on a one-time or repeated basis based upon the judgment of a medical professional.

The reevaluation procedure 220 may itself involve one or more steps of the method 200. Through a reevaluation procedure 220, it may be determined that one or more patient symptoms may be better, successfully, or adequately treated or managed in accordance with a different pulse repetition frequency function; a lower peak intensity or amplitude; less frequent neural stimulation; a modified configuration of elements within the set of electrodes 140 and/or modified signal polarities applied thereto; lower dosage and/or less frequent drug therapy; and/or other variations in or modifications to the ongoing treatment protocol. As further described below with reference to FIG. 6, a reevaluation procedure 220 that indicates that better, successful, or adequate treatment or management of one or more patient symptoms may be achieved with less intense and/or less frequent neural stimulation may be indicative of compensatory, restorative, and/or rehabilitative neuroplastic change within the patient 190.

Figure 4:
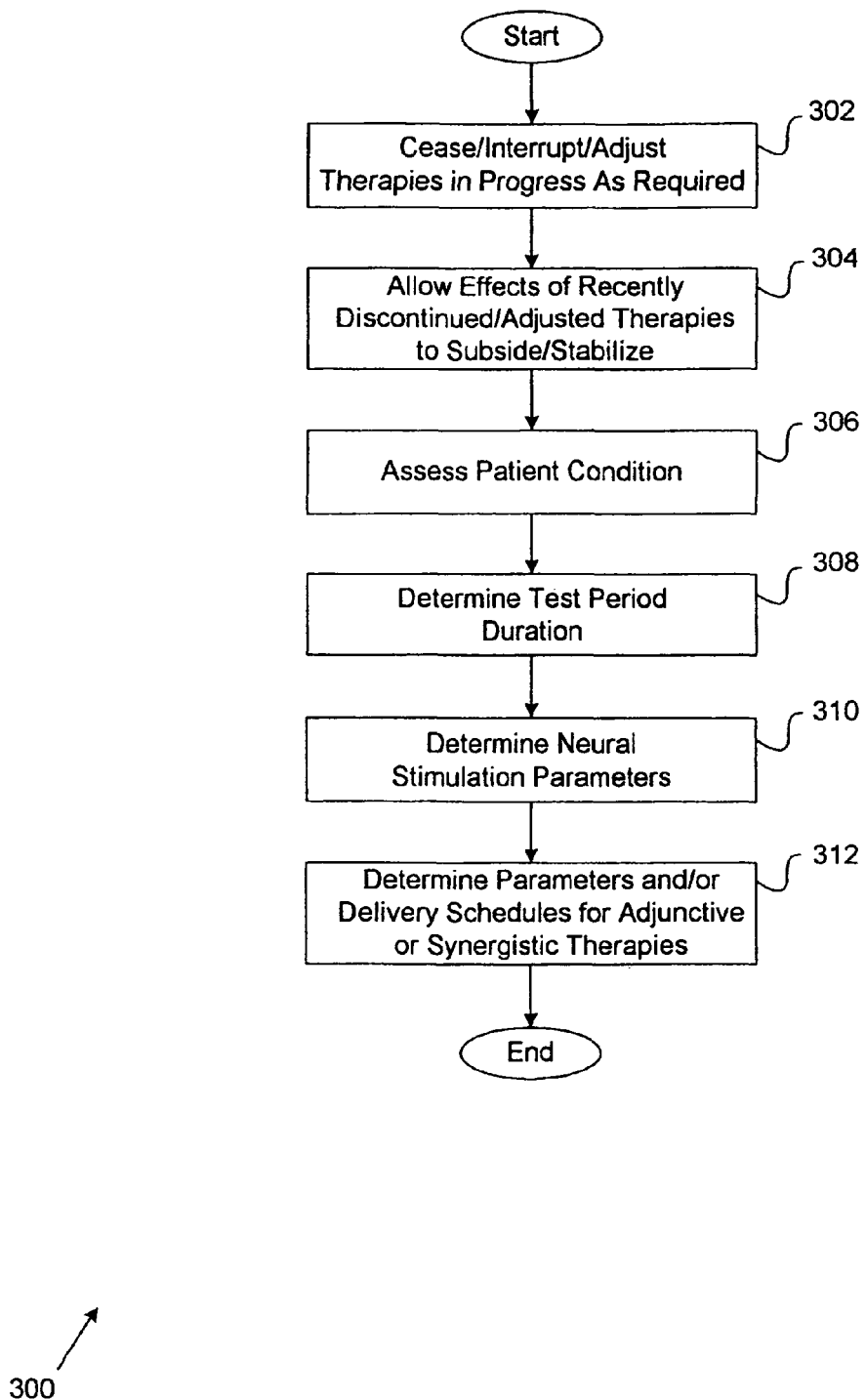
FIG. 4 is a flowchart illustrating various methods for establishing, adjusting, or adapting a test protocol according to an embodiment of the invention.

FIG. 4 is a flowchart illustrating various methods for establishing, adjusting, or adapting a test protocol according to an embodiment of the invention. Such methods may be used in the test protocol management procedure 206 of FIG. 3. In one embodiment, a method 300 includes an adjustment procedure 302 that involves adjustment, cessation, or interruption of patient therapies currently in progress as required. Such therapies may comprise neural stimulation and/or one or more adjunctive therapies such as a drug therapy. The method 300 may also include a waiting procedure 304 during which effects of recently adjusted, discontinued, or interrupted therapies are allowed to subside, stabilize, or "wash out." The waiting procedure 304 may maximize or increase a likelihood that a previously applied therapy has a minimal or negligible effect upon an upcoming test therapy (i.e., no carry-over effects). The method 300 may further include an assessment procedure 306 that involves assessment, qualification, and/or quantification of the severity of one or more patient symptoms, possibly to establish a baseline or reference patient condition.

The method 300 may additionally include a duration establishment procedure 308 that involves determination or definition of a test period duration during which a test therapy may be applied to the patient 190. A test period duration may be short or relatively short, for example, approximately 1 or more minutes or hours, to facilitate efficient determination of the effectiveness of a test protocol upon acute or readily responsive patient symptoms. Alternatively, a test period duration may be relatively long, for example, approximately 1 or more days, weeks, or even months, to facilitate determination of the effectiveness of a test protocol upon patient symptoms having slower or prolonged treatment response characteristics. The method 300 may further include a first test protocol definition procedure 310 that involves determination, selection, and/or specification of neural stimulation parameters that comprise one or more portions of the test protocol. The method 300 may additionally include a second test protocol definition procedure 312 that involves determination or definition of a set of parameters corresponding to one or more adjunctive therapies that may form a portion of the test protocol. Such parameters may include, for example, a drug dosage and delivery schedule.

Figure 5:
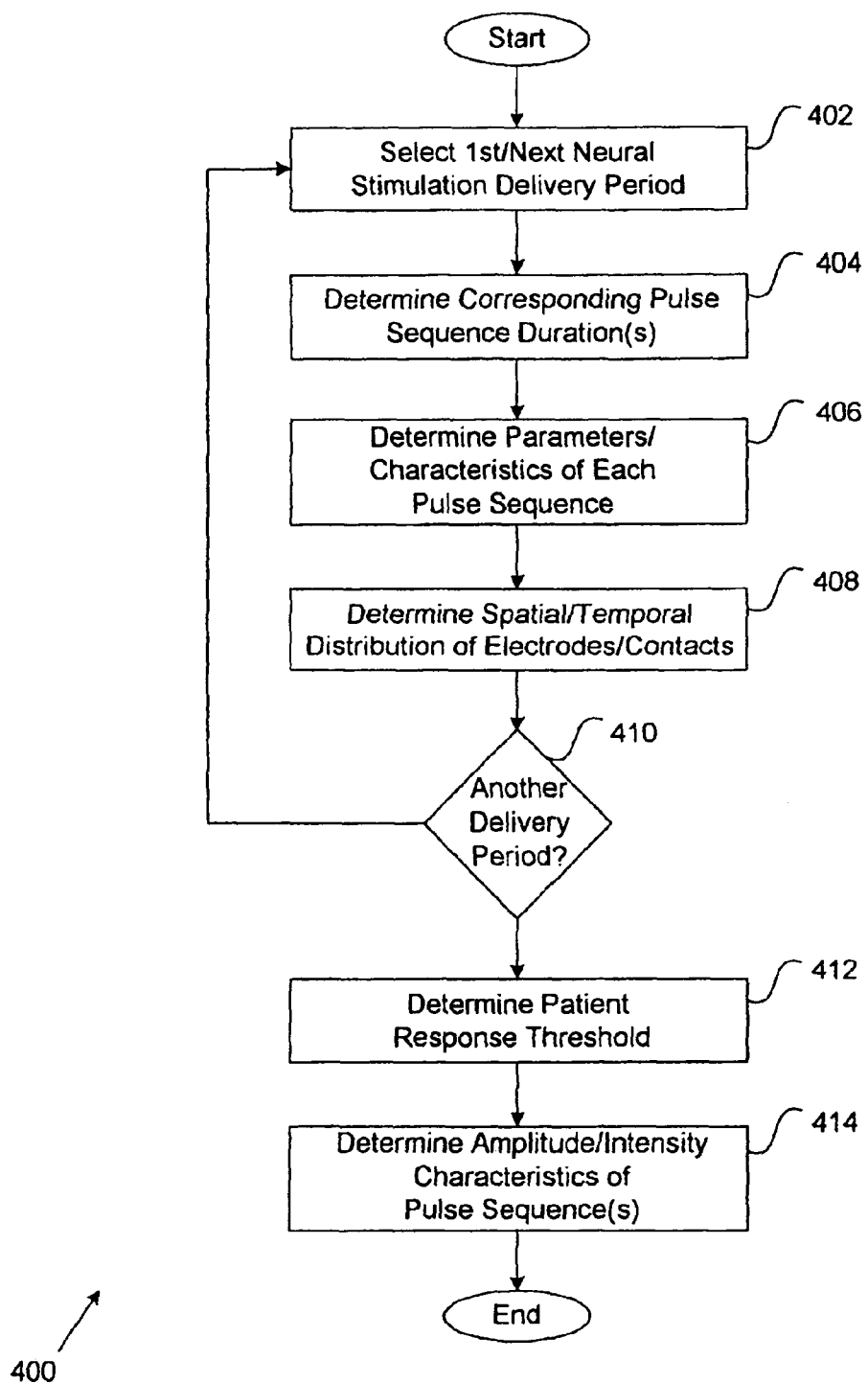
FIG. 5 is a flowchart illustrating various methods for determining neural stimulation parameters according to an embodiment of the invention.

FIG. 5 is a flowchart illustrating various methods for determining neural stimulation parameters according to an embodiment of the invention. Such methods may be used in the first test protocol definition procedure 310 of FIG. 4. In one embodiment, a method 400 includes a delivery period selection procedure 402 that involves determination or selection of a first or next time interval within the current test period that neural stimulation may be delivered to the patient 190. The method 400 may further include a pulse sequence duration procedure 404 that involves selection and/or specification of one or more pulse sequence durations and/or quiescent intervals within and/or between pulse sequences for the neural stimulation delivery period currently under consideration. The method 400 may accommodate multiple pulse sequences, variable types of pulse train sequences, and/or quiescent intervals between pulse sequences to provide enhanced flexibility with respect to establishing test protocols that may be useful for efficiently treating symptoms of various disorders.

Relative to treating PD symptoms, stimulation that reduces the output activity of the globus pallidus internalis (GPi) can be highly beneficial. Deep Brain Stimulation (DBS) research has shown that stimulation delivered to the globus pallidus internalis (GPi) may significantly reduce GPi activity over a period that can last several seconds beyond the termination of such stimulation. For example, a continuous or essentially continuous pulse train lasting 3 seconds may result in reduced or significantly reduced GPi output activity that lasts approximately 1.5 seconds beyond termination of the 3 second pulse train. Delivering or applying neural stimulation to one or more target neural populations having synaptic projections into the GPi or associated neural circuitry such that pulse sequences or pulse trains are separated by one or more appropriate quiescent intervals may therefore maintain or sustain reduced GPi activity while eliminating the need to deliver continuous stimulation. Delivery of neural stimulation in such a manner advantageously reduces power consumption. Thus, a pulse sequence comprising periodic pulse trains lasting approximately 3 seconds separated by quiescent intervals lasting approximately 1.5 seconds may provide significant therapeutic benefit in a power efficient manner.

The method 400 may additionally include a waveform definition procedure 406 that involves selection and/or specification of a set of waveform parameters that define or describe each pulse sequence currently under consideration. Such waveform characteristics may include a pulse repetition frequency or frequency function, a pulse amplitude decay function, and/or other pulse sequence parameters. Depending upon embodiment details and/or current symptoms under consideration, the pulse repetition frequency may vary within any given pulse sequence, and/or from one pulse sequence to another. By accommodating such variation, the method may facilitate the definition of a test protocol or an arrived-at ongoing treatment protocol that includes multiple pulse repetition frequencies, where particular individual pulse frequencies or pulse frequency subsets may be directed toward maximizing or enhancing the effectiveness of neural stimulation in treating particular PD and/or movement disorder symptoms. As an illustrative example, if (a) a pulse repetition frequency of approximately 25 Hz appears optimal or nearly optimal for treating tremor, (b) a pulse repetition frequency of approximately 30 Hz appears optimal for treating rigidity, and (c) a pulse repetition frequency of approximately 15 Hz appears optimal for treating bradykinesia, then a test protocol or an ongoing treatment protocol may call for neural stimulation that periodically alternates between these pulse repetition frequencies in accordance with given neural stimulation delivery periods and possibly including one or more quiescent periods therebetween. Alternatively, the test protocol or the ongoing treatment protocol may call for neural stimulation that sweeps between 15 and 30 Hz in a continuous or nearly continuous manner.

In general, a test protocol may call for neural stimulation having one or more pulse repetition frequencies specified in accordance with a temporal and/or mathematical function that is based upon individual pulse repetition frequencies determined to be optimal or near-optimal for treating particular subsets of patient symptoms. Such a temporal and/or mathematical function may be based upon the nature and/or severity of such symptoms. For example, if the patient's baseline or reference state indicates that the patient experiences tremor in a significantly more severe manner than bradykinesia, a test protocol may call for neural stimulation in which an amount of time spent delivering stimulation optimized or nearly optimized for treating tremor exceeds an amount of time spent delivering stimulation optimized or nearly optimized for treating bradykinesia. Additionally or alternatively, the test protocol may call for neural stimulation having a frequency function that is weighted or biased relative to individually determined frequencies corresponding to particular symptom subsets. Such a test protocol may call for neural stimulation that delivers, for example, a combined frequency of 27 Hz for treating both tremor and rigidity, as well as a pulse repetition frequency of 15 Hz for treating bradykinesia. Furthermore, a test protocol may call for neural stimulation having a pulse repetition frequency function that depends upon one or more treatment response times associated with particular symptoms, and/or one or more time intervals that relief from particular symptoms persists in the absence of neural stimulation.

The method 400 may further include an electrode element selection procedure 408 that involves identifying or defining a spatial and/or temporal distribution of electrodes 142 and/or contacts 144 to which neural stimulation may be directed during the delivery period under consideration. The electrode element selection procedure 408 may alternatively or additionally select or define signal polarities corresponding to particular electrodes 142 and/or contacts 144 relative to one or more portions of the test period. In the event that a current test period includes more than one delivery period, the method 400 may return to the delivery period selection procedure 402.

The method 400 may also include a threshold determination procedure 412 that involves determination of a minimum or near minimum neural stimulation amplitude or intensity that evokes or induces a given type of patient response, reaction, behavior, and/or sensation. A neural stimulation threshold may be determined by successively applying higher amplitude neural stimulation signals to the patient 190 until an observable or detectable response occurs. Each threshold determination attempt may apply a limited duration neural stimulation signal to the patient 190, for example, a pulse sequence lasting 0.5 seconds, 1 second, 3 seconds, or some other length of time. A waiting, quiescent, or washout period between successive threshold determination attempts, during which the patient 190 receives no neural stimulation, may ensure that each threshold determination attempt is independent or essentially independent of residual effects associated with previously applied signals. A quiescent period may span several seconds to one or more minutes, for example, approximately one minute. In one embodiment, the threshold determination procedure 412 involves determination of a motor, movement, or motion threshold through motion detection techniques and/or visual observation. In another embodiment, the threshold determination procedure 412 may involve determination of an EMG threshold and/or another type of neural stimulation threshold.

The method 400 may further include an amplitude determination procedure 414 that involves determination or selection of peak or average amplitudes or intensities corresponding to the set of pulse sequences defined or specified within the current test period based upon the results or outcome of the threshold determination procedure 412. Depending upon embodiment details, a peak pulse sequence amplitude may be defined as a given percentage of a neural stimulation threshold, for example, 50% of a movement threshold or 70% of an EMG threshold. In some embodiments, different pulse sequences within a delivery period or test period may have different peak amplitudes.

Figure 6:
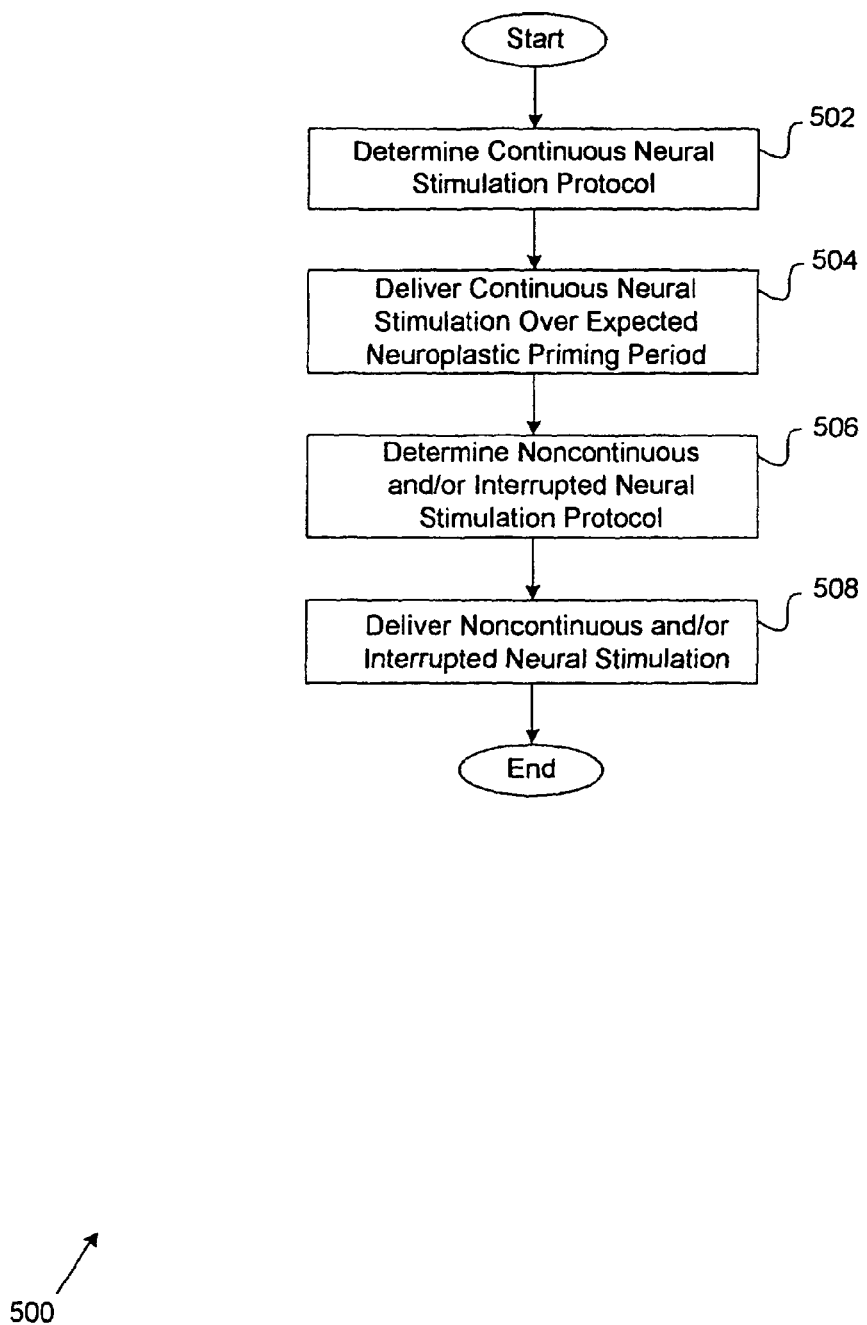
FIG. 6 is a flowchart illustrating various methods for modifying, adjusting, or adapting neural stimulation therapy in view of a likelihood or possibility of a lasting or long term neuroplastic change occurring within a patient over time.

FIG. 6 is a flowchart illustrating various methods for modifying, adjusting, or adapting neural stimulation therapy in view of a likelihood or possibility of a lasting or long term neuroplastic change occurring within a patient 190 over time. Such methods may involve the reevaluation procedure 220 and/or other procedures described above with in association with FIG. 3. The propensity of a given neural population to undergo neuroplastic change may depend upon the application of an initial neural stimulation regimen to the neural population in a particular manner, such as a continuous, generally continuous, or frequent manner over a given or minimum amount of time. This may in turn facilitate or effectuate initiation and reinforcement of chemical and/or structural adaptations or changes in the neural population and/or neural circuitry associated therewith, thereby "priming" the neural population to accept and/or maintain long term or lasting neuroplastic change.

As an illustrative example, depending upon symptom type and severity, effective or generally effective treatment of PD or other movement disorder symptoms may initially require continuous, essentially continuous, or nearly continuous neural stimulation for a neuroplastic priming period of approximately one month. After such a neuroplastic priming period, however, effective treatment of one or more symptoms may require stimulation for a limited number of hours per day, such as during the patient's normal waking hours. Alternatively, effective treatment may require continuous stimulation for approximately 30 minutes, after which treatment may be interrupted for approximately 30 minutes, and so on. In another embodiment, the stimulation can be applied on a twenty four hour basis for an initial period and then on a reduced basis for a subsequent period. The stimulation, for example, can be applied all throughout each day for an initial period of approximately one month, and then it can be applied only during waking hours after the initial period. This is expected to provide sufficient results in many situations and conserve battery life.

One method 500 for modifying, adjusting, or adapting neural stimulation therapy in view of a likelihood or possibility of a lasting or long term neuroplastic change may include a first stimulation optimization or refinement procedure 502 that involves determination of a continuous neural stimulation protocol for treating one or more patient symptoms. The method 500 may further include a continuous stimulation procedure 504 that involves delivery or application of neural stimulation to the patient 190 in accordance with the continuous neural stimulation protocol for a predetermined time period, for example, one or more weeks or one or more months. The predetermined time period may correspond to an expected or likely neuroplastic priming period. The method 500 may additionally include a second stimulation optimization or refinement procedure 506 that involves determination of a noncontinuous and/or periodically interrupted neural stimulation protocol for treating patient symptoms under consideration. The method 500 may also include a noncontinuous or interrupted stimulation procedure that involves delivery of noncontinuous and/or interrupted neural stimulation to the patient 190 in accordance with the noncontinuous and/or interrupted neural stimulation protocol. The first and/or second stimulation optimization or refinement procedures 502, 506 may include or encompass one or more procedures described above in association with FIG. 3. Additionally, the second stimulation optimization or refinement procedure 506 may be repeated following application of noncontinuous or interrupted stimulation to the patient 190 for a given amount of time.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

The invention claimed is:

1. A method of treating Parkinson's disease (PD) in a patent, the method comprising:
generating electrical stimulation pulses from a pulse generator, the electrical stimulation pulses comprising a plurality of groups of pulses occurring according to a burst frequency, wherein (i) multiple pulses are generated within each respective group according to a pulse repetition frequency, (ii) adjacent groups within the plurality of groups are spaced apart from each other in time with a substantially quiescent period, and (iii) the generating is repeated for a limited number of hours per day such that the generating is performed at most for 50% of a respective day, wherein each group in the plurality of groups is less than three (3) seconds and each quiescent period is less than one (1) minute; and
applying the plurality of groups of pulses to a target neuronal population of the patient using one or more electrodes of one or more electrical leads implanted within a deep brain location of the patient, wherein (i) the one or more electrodes are within the globus pallidus internalis (GPi) or within the subthamalic nucleus (STN), and (ii) the applying causes the patient to experience a change in neuronal circuitry from a disease state that results in reduced PD-related tremor or PD-related bradykinesia in the patient while the electrical stimulation pulses are not applied.

2. The method of claim 1 wherein the applying causes the patient to experience improved motor functioning while the electrical stimulation pulses are applied.

3. The method of claim 1 wherein the pulse frequency is adapted to affect at least one motor symptom of PD in the patient.

4. The method of claim 1 wherein improved motor functioning is experienced by the patient for at least thirty minutes without stimulation after the applying is performed.

5. The method of claim 4 wherein the patient experiences reduced tremor for at least thirty minutes without stimulation after the applying is performed.

6. The method of claim 1 wherein respective groups of multiple pulses are applied to different electrodes of multiple electrodes at different points in time according to a pre-defined temporal distribution.

7. The method of claim 1 wherein the generating comprises:
cycling between (i) an on-period in which the groups of electrical pulses are generated for a first defined amount of time and (ii) an off-period in which electrical pulses are not generated for a second defined amount of time, wherein the first and second amounts of time are approximately equal.

8. The method of claim 1 wherein the groups of pulses comprise monopolar pulses.

9. The method of claim 1 wherein the groups of pulses comprise biphasic, charge-balanced pulses.

10. The method of claim 1 wherein the change in neuronal circuitry results in a reduction in a neuronal output of the GPi of the patient.

11. A method of treating Parkinson's disease (PD) in a patent, the method comprising:
for a first time period, applying a first electrical deep brain stimulation regimen to the patient for neuroplastic priming to cause a change in neuronal circuitry from a disease state, wherein the first time period extends for at least multiple days; and
after the first time period, applying a second electrical deep brain stimulation regimen to the patient wherein (i) the second electrical deep brain stimulation regimen employs a reduced amount of time of application of electrical stimulation to the patient per day relative to the first electrical deep brain stimulation regimen, and (ii) the second electrical deep brain stimulation regimen comprises:
(a) generating electrical stimulation pulses from a pulse generator, the electrical stimulation pulses comprising a plurality of groups of pulses occurring according to a burst frequency, wherein (i) multiple pulses are generated within each respective group according to a pulse repetition frequency, and (ii) adjacent groups within the plurality of groups are spaced apart from each other in time with a substantially quiescent period, wherein each group in the plurality of groups lasts less than three (3) seconds and each quiescent period lasts less than one (1) minute; and
(b) applying the plurality of groups of pulses to a target neuronal population of the patient using one or more electrodes of one or more electrical leads implanted within a deep brain location of the patient, wherein (i) the one or more electrodes are within the globus pallidus internalis (GPi) or within the subthamalic nucleus (STN), and (ii) the applying causes the patient to maintain or experience a change in neuronal circuitry from a disease state that results in reduced PD-related tremor or PD-related bradykinesia in the patient while the electrical stimulation pulses are not applied for a period of time of at least thirty (30) minutes after application of the plurality of groups of pulses.

12. The method of claim 11 wherein the applying the plurality of groups causes the patient to experience improved motor functioning while the electrical stimulation pulses are applied.

13. The method of claim 11 wherein the pulse frequency is adapted to affect at least one motor symptom of PD in the patient.

14. The method of claim 11 wherein respective groups of multiple pulses are applied to different electrodes of multiple electrodes at different points in time according to a pre-defined temporal distribution.

* * * * *